United States Patent [19]

Kim et al.

[11] Patent Number: 4,906,460

[45] Date of Patent: Mar. 6, 1990

[54] ADDITIVE FOR HAIR TREATMENT COMPOSITIONS

[75] Inventors: Wendy W. Kim, Salt Lake City; Sherman L. Kendall, Park City, both of Utah

[73] Assignee: Sorenco, Salt Lake City, Utah

[21] Appl. No.: 228,998

[22] Filed: Aug. 5, 1988

[51] Int. Cl.$^4$ .......................... A61K 7/06; A61K 7/09
[52] U.S. Cl. ........................................ 424/70; 424/72; 514/773
[58] Field of Search ..................... 424/70, 72; 514/773, 514/774

[56] References Cited

U.S. PATENT DOCUMENTS

| | | | |
|---|---|---|---|
| 4,793,992 | 12/1988 | Mathews et al. | 424/70 |
| 4,798,722 | 1/1989 | Edman et al. | 424/72 |

OTHER PUBLICATIONS

Cosmetics & Toiletries, vol. 103, Mar. 1988, p. 77.
Cosmetics & Toiletries, vol. 103, May 1988, pp. 19, 94.

*Primary Examiner*—Ellis P. Robinson
*Assistant Examiner*—Susan S. Rucker
*Attorney, Agent, or Firm*—Trask, Britt & Rossa

[57] ABSTRACT

An additive for hair treatment compositions includes soluble animal keratin in admixture with hydrolyzed animal collagen and silk amino acids.

8 Claims, No Drawings

ADDITIVE FOR HAIR TREATMENT COMPOSITIONS

BACKGROUND OF THE INVENTION

1. Field:

This invention pertains to hair treatment. It is specifically directed to an additive for water-based hair treatment compositions and provides a protein-based additive including keratin, collagen and amino acids.

2. State of the art:

The formulation of hair treatment compositions such as shampoos; setting lotions, sprays and dressings; tonics and conditioners; colorants; permanent wave solutions and strengtheners; and straighteners is a well developed art. The textbook *Harry's Cosmeticology*, edited by J. B. Wilkinson and R. J. Moore, Chemical Publishing Company, New York (Seventh edition, 1982) includes an approximately 200 page section devoted to human hair, its structure, nutrition and care. This text discloses the common constituents of all of the aforementioned hair treatment compositions and the practical considerations involved in their formulation and application. Each of the several chapters devoted to specific categories of compositions; e.g., shampoos, ends with a bibliography of references pertinent to that category. Other portions of the book describe product ingredients; e.g., surface active agents, antioxidants and emulsions, as well as their selection and incorporation in hair treatment products. This book and its bibliographies disclose the state of the art pertaining to the manufacture and application of hair treatment products and are incorporated by reference to the extent that their respective teachings are applicable to this disclosure.

The Cosmetic, Toiletry and Fragrance Association, Inc. of Vermont Avenue, N.W., Washington, D.C. 20005 publishes a CTFA cosmetic ingredient dictionary. References in this disclosure to CTFA names correspond to the names listed in the third edition (1982) of that dictionary.

Among the constituents which are currently available to formulators of hair treatment compositions is a class known as "soluble keratin." The materials of this class which are of most interest to hair treatment are those referred to within the CTFA adopted name system of nomenclature as "soluble animal keratin" which have molecular weights greater than about 100,000. An exemplary such material is that sold under the trademark "KERASOL" by Croda, Inc., 183 Madison Avenue, New York, New York. "KERASOL" has a molecular weight of about 125,000, and a structure which approximates that of human hair. It is soluble in water and is typically supplied as a 15 percent active ingredients aqueous solution. It has been incorporated into a wide range of water-based hair care products, including permanent wave solutions, shampoos and conditioners, although in shampoos and conditioners it will not covalently bond to the hair. Nevertheless, its film-forming properties are known to improve the body and sheen, as well as the manageability and combing characteristics, of hair.

Another family of protein compounds used by formulators of hair treatment compositions is the protein quaternary compounds with specific gravities greater than about 1. Croda, Inc. supplies a representative such compound under the trademark "CROQUAT M." This product is a viscous amber liquid containing about 40 to about 45 percent by volume cocoyl quaternized protein, the remaining volume consisting of volatiles. It is water soluble, and in 10 percent aqueous solution has a pH in the range of about 4 to about 5.5. Its CTFA adopted name is "cocodimonium hydrolyzed animal collagen."

It is known that the hydrolysis of pure silk fiber can produce a mixture of the individual amino acids which naturally occur in silk ("silk amino acids"). The major such silk amino acids are glycine, alanine, serine, and tyrosine. The silk amino acid mixture resulting from silk hydrolysis is of low molecular weight and of specific gravity above about 1. Croda, Inc. supplies a silk amino acid mixture under the tradename "CROSILK LIQUID" which typically has a solids content in the range of about 27 to about 31 percent by weight and an ash content of about 12 to about 16 percent by weight. A typical amino acid spectrum of "CROSILK LIQUID" is reported in Table A.

TABLE A

| Amino Acid | Percent by Weight |
| --- | --- |
| ALANINE | 28.4 |
| GLYCINE | 34.7 |
| VALINE | 2.0 |
| LEUCINE | 1.2 |
| PROLINE | 1.2 |
| TYROSINE | 0.6 |
| PHENYLALANINE | 0.9 |
| SERINE | 15.4 |
| THREONINE | 1.9 |
| ARGININE | 1.5 |
| ASPARTIC ACID | 4.7 |
| GLUTAMIC ACID | 4.1 |
| ISOLEUCINE | 0.8 |
| LYSINE | 1.4 |
| HISTIDINE | 0.8 |
| CYSTINE | 0.1 |
| METHIONINE | 0.2 |
| | 99.9 |

SUMMARY OF THE INVENTION

It has been found that the benefits of soluble animal keratin for hair treatment can be enhanced by incorporating it in admixture with hydrolyzed animal collagen and silk amino acids, in appropriate proportions, in a variety of water-based hair treatment compositions; most notably shampoos, conditioners, and permanent wave preparations.

The benefits of this invention can be realized by formulating an additive comprising the keratin, collagen and amino acid constituents for subsequent blending with available "off-the-shelf" hair treatment products. Such an additive has particular application in a commercial hair styling setting. A small amount of the additive may be added, for example, to a conventional permanent wave solution just prior to application. Even though the permanent wave solution is processed in accordance with its usual manufacturer-recommended procedure, the presence of the additive improves the resulting hair strength and volume.

In other circumstances, the additive or its ersatz equivalent may be incorporated directly into the hair treating composition as distributed at retail or to the trade. Shampoos and conditioners are enhanced by the inclusion of the keratin-collagen-amino acid admixture of this invention, whether preformulated or by the inclusion in the composition of the individual constituents of the additive. The term "additive" is used in this disclosure and the appended claims to include both modes of formulation.

The principal ingredient of the admixture may be regarded as water-soluble animal keratin, e.g. the composition commercially sold under the trademark "KERASOL." On a weight percent basis, the collagen and amino acid constituents are each present in an amount of between about ten and about 100 percent of the amount of keratin present in the admixture. The collagen constituent should be a water-soluble hydrolyzed animal collagen such as that sold under the trademark "CROQUAT M," and typically comprises about ten to about 25 percent by weight of the additive. The amino acid constituent should predominate in the amino acids found in natural silk, and typically comprises about eight to about 25 percent by weight of the additive. The liquid sold under the trademark "CROSILK LIQUID" is considered to represent a preferred source of silk amino acids.

Each of the three essential constituents of the additive is normally supplied as an aqueous solution or water soluble liquid. The solids, or active ingredients of these liquids, are generally about ten to about 20 percent in the case of keratin, approximately twice that amount in the case of the amino acids, and about three times that amount (about 30 to about 60 percent) in the case of collagen. Moreover, other constituents may be included in the additive in accordance with conventional formulation techniques to contribute other desirable characteristics.

DESCRIPTION OF PREFERRED EMBODIMENTS

An additive for permanent wave solutions may be formulated by simply mixing weight quantities of the three essential components as supplied in liquid form by Croda, Inc., New York, N.Y., according to Table B.

TABLE B

| Trademark (Croda, Inc.) | Description | Weight Percent Range |
| --- | --- | --- |
| KERASOL | 15 percent soluble animal keratin | 60-90 |
| CROQUAT M | 45 percent hydrolyzed animal collagen | 5-20 |
| CROSILK LIQUID | 30 percent silk amino acids | 5-20 |

In use, approximately ⅓ ounce of any such formulation is sufficient for use with the quantity of permanent wave solution required for one individual permanent wave. As compared to the use of keratin alone, the additive of this invention contributes strength and flexibility, especially to weak, limp or damaged hair. The keratin forms covalent bonds with the cystine linkage of the hair, thereby adding volume to individual hair shafts.

EXAMPLE 1

A typical practical additive for permanent wave solutions is formulated by mixing the components described in Table B and a minor amount of a preservative, such as that sold by Sutton Laboratories, Inc., Chatham, N.J., under the trademark "GERMABEN II,"

| Constituent | Weight Percent |
| --- | --- |
| KERASOL | 79 |
| CROQUAT M | 10 |
| CROSILK LIQUID | 10 |
| GERMABEN II | 1 |

Additives for shampoos and conditioners may be formulated from the components described in Table B. The additive components will usually be present as constituents of the shampoo or conditioner in association with a host of other conventional constituents. The additive itself will typically comprise between about one to about 15 percent of the hair treatment composition by weight. Conventional hair treatment compositions need not be otherwise modified.

EXAMPLE 2

A typical shampoo composition which includes the additive of this invention has the following composition by weight. The constituents not described in Table B or Example 1 are listed by their CTFA names, and may be more specifically identified by reference to the CTFA cosmetic ingredient dictionary:

| Trade Name | CTFA Name | Weight Percent |
| --- | --- | --- |
| Sulfotex UBL 100 Acid | Dedecybenzene Sulfonic Acid | 2.92 |
| Triethanolamine | Triethanolamine | 1.74 |
| DI Water | | 49.16 |
| Crotein HKP | Keratin Amino Acid (and) Sodium Chloride | 0.4 |
| Panthenol | Panthenol | 0.24 |
| Sulfotex LMSE | Sodium Laureth Sulfate | 14.0 |
| Sulfotex WA | Sodium Laryl Sulfate | 8.0 |
| Germaben II | Propylene Glycol 56% Diazolidinyl Urea 30% Methyl Paraben 11% Propyl Paraben 3% | 1.0 |
| Ninol LL-50 | Lauramide DEA | 7.0 |
| Kerasol | Soluble Animal Keratin | 10.0 |
| Crosilk Liquid | Silk Animo Acids | 1.25 |
| Croquat M | Cocodimonium Hydrolyzed Animal Collagen | 1.25 |
| DC 929 | Amodimethicone (and) Nonoxynol-10 (and) Tallowdimonium Chloride | 1.0 |
| D & C Yellow #5 Solution | | 0.04 |
| Clindrol SEG | Glycol Stearate (optional) | 2.0 |
| Fragrance (Lauren Fragrance, Functional) | | qs |

EXAMPLE 3

A typical hair conditioning solution which includes an additive of this invention has the following composition by weight. The constituents not described on Table B or in Example 1 are listed by their CTFA names, and may be more specifically identified by reference to the CTFA cosmetic ingredient dictionary.

| Trade Name | CTFA Name | Weight Percent |
| --- | --- | --- |
| DI Water | | 87.92 |
| Kerasol | Soluble Animal Keratin | 0.5 |
| Adogen | Quatermium 18 | 4.5 |
| Natrasol 250 HR | Hydroxyethylcellulose | 0.18 |
| DC 200 | Dimethicone | 0.2 |
| Croquat M | Cocodimonium Hydrolyzed Animal Collagen | 0.2 |
| Crosilk Liquid | Silk Amino Acid | 0.2 |

-continued

| Trade Name | CTFA Name | Weight Percent |
|---|---|---|
| Panthenol | Panthenol | 0.2 |
| Cetyl Alcohol | Cetyl Alcohol | 1.2 |
| Steryl Alcohol | Steryl Alcohol | 0.5 |
| Clindrol SEG | Glycol stearate | 1.5 |
| Lipocol | Cetheareth-20 | 0.5 |
| Mazeen S-13 | Stearamidopropyl dimethylamine | 0.5 |
| Lexemul 515 | Glyceryl stearate | 0.8 |
| DC 929 | Amodimethicone (and) nonoxynol-10 (and) tallowtrimonium chloride | 1.0 |
| Kathone CG | Methylchloroisothiazolinone (and) methylisothiazolinone | 0.1 |
| Crotein WKP | Keratin Pentapeptide | 0.001 |
| Fragrance | | qs |

A normal range by weight of the constituents of Table B (or their equivalents) in shampoo or conditioner formulations by weight percent is reported in Table C.

TABLE C

| Constituent (Table B) | Weight Percent Range |
|---|---|
| KERASOL | 0.2-10 |
| CROQUAT M | 0.2-20 |
| CROSILK LIQUID | 0.2-10 |

Inclusion of the additives of this invention in shampoos, conditioners and other hair treatment compositions in addition to permanent wave solutions extends the benefits of keratin additions, (as enhanced by the conclusion of collagen and amino acids) during the permanent wave treatment. Accordingly, the practice of this invention offers a long-term hair care regime which reduces or mollifies the damage otherwise associated with hair permanent wave treatments.

Reference herein to the specific details of certain preferred embodiments are not intended to restrict the scope of the appended claims.

What is claimed is:

1. An additive for water-based hair treatment compositions, comprising a mixture of:

a water soluble animal keratin with a molecular weight above about 100,000;

a water soluble hydrolyzed animal collagen with a specific gravity above about one, present in an amount between about ten and about 100 percent by weight, based upon the weight of said animal keratin in said mixture; and a silk amino acid with a specific gravity above about one, present in an amount between about eight and about 100 percent by weight, based upon the weight of said animal keratin in said mixture.

2. An additive according to claim 1 wherein the animal keratin has a molecular structure which approximates that of human hair.

3. An additive according to claim 2 wherein the hydrolyzed animal collagen is cocodimonium hydrolyzed animal collagen.

4. An additive according to claim 2 wherein the silk amino acid is present in an admixture derived by the hydrolysis of silk fiber.

5. An additive according to claim 4 wherein said water soluble hydrolyzed animal collagen is present in an amount between about ten and about 25 weight percent.

6. An additive according to claim 5 wherein said silk amino acid is present in an amount between about eight and about 25 weight percent.

7. An additive according to claim 1 wherein said animal keratin is present in an aqueous solution, containing about ten to about 20 percent active ingredients, said animal collagen is present in a liquid preparation containing between about 30 and about 60 percent solids and said silk amino acid is present as an aqueous solution containing about 20 to about 40 percent solids.

8. An additive according to claim 7 wherein said keratin-containing aqueous solution is present in an amount between about 60 and about 90 weight percent, said collagen containing liquid is present in an amount between about five and about 20 weight percent and said amino acid-containing solution is present in an amount between about five and about 20 weight percent.

* * * * *